United States Patent
Egawa

(10) Patent No.: US 6,386,357 B1
(45) Date of Patent: May 14, 2002

(54) SOFT INTRAOCULAR LENS-FOLDING DEVICE AND STORAGE CASE

(75) Inventor: Yoshikazu Egawa, Tokyo (JP)

(73) Assignee: Hoya Healthcare Corporation, Tokyo (JP)

( * ) Notice: Subject to any disclaimer, the term of this patent is extended or adjusted under 35 U.S.C. 154(b) by 0 days.

(21) Appl. No.: 09/701,967

(22) PCT Filed: Jun. 12, 2000

(86) PCT No.: PCT/JP00/04648

§ 371 Date: Dec. 6, 2000

§ 102(e) Date: Dec. 6, 2000

(87) PCT Pub. No.: WO01/03611

PCT Pub. Date: Jan. 18, 2001

(30) Foreign Application Priority Data

Jul. 12, 1999 (JP) .............................. 11-197629

(51) Int. Cl.⁷ .............................. A45C 11/04; A61F 9/00
(52) U.S. Cl. .............................. 206/5.1; 606/1; 606/107; 623/6
(58) Field of Search .............................. 206/5.1; 606/1, 606/106, 107, 205; 623/6

(56) References Cited

U.S. PATENT DOCUMENTS

| | | | |
|---|---|---|---|
| 5,100,410 A | | 3/1992 | Dulebohn |
| 5,139,501 A | | 8/1992 | Klass |
| 5,171,241 A | * | 12/1992 | Buboltz et al. ............ 606/1 |
| 5,176,686 A | * | 1/1993 | Poley ............ 606/107 |
| 5,281,227 A | * | 1/1994 | Sussman ............ 606/107 |
| 5,290,293 A | * | 3/1994 | Van Noy et al. ............ 606/107 |
| 5,454,818 A | * | 10/1995 | Hambleton et al. ............ 606/107 |
| 5,578,042 A | * | 11/1996 | Cumming ............ 606/107 |
| 5,947,974 A | * | 9/1999 | Brady et al. ............ 606/107 |
| 6,007,542 A | * | 12/1999 | Duprat ............ 606/107 |
| 6,129,733 A | * | 10/2000 | Brady et al. ............ 606/107 |
| 6,142,999 A | * | 11/2000 | Brady et al. ............ 606/107 |

FOREIGN PATENT DOCUMENTS

| | | |
|---|---|---|
| JP | 4-212350 | 8/1992 |
| JP | 4-309348 | 10/1992 |
| JP | 5-103803 | 4/1993 |
| JP | 9-501574 | 2/1997 |
| JP | 11-169391 | 6/1999 |
| WO | WO 95/00081 | 1/1994 |

\* cited by examiner

*Primary Examiner*—Bryon P. Gehman
(74) *Attorney, Agent, or Firm*—Oliff & Berridge PLC

(57) ABSTRACT

A soft intraocular lens-folding device comprises a movable member 1 and a base member 2. The movable member 1 comprises an elastically bendable pair of legs 12a, 12b, and a common base 11 for connecting this pair of legs 12a, 12b. At the tips of the pair of legs 12a, 12b there is disposed lens-receiving portions 13a, 13b, and wall portions 14a, 14b. In the lens-receiving portions 13a, 13b, a soft intraocular lens 3 is set astride both legs. The wall portions 14a, 14b have the function of clamping a soft intraocular lens 3 set in the lens-receiving portions 13a, 13b. The bass member 2 comprises a slide groove portion 21. This slide groove portion 21 is formed so as to allow the tips of the pair of legs 12a, 12b to penetrate and elide through, and, in addition, to narrow the gap of the pair of legs 12a, 12b in accordance with the extent of movement thereof.

27 Claims, 4 Drawing Sheets

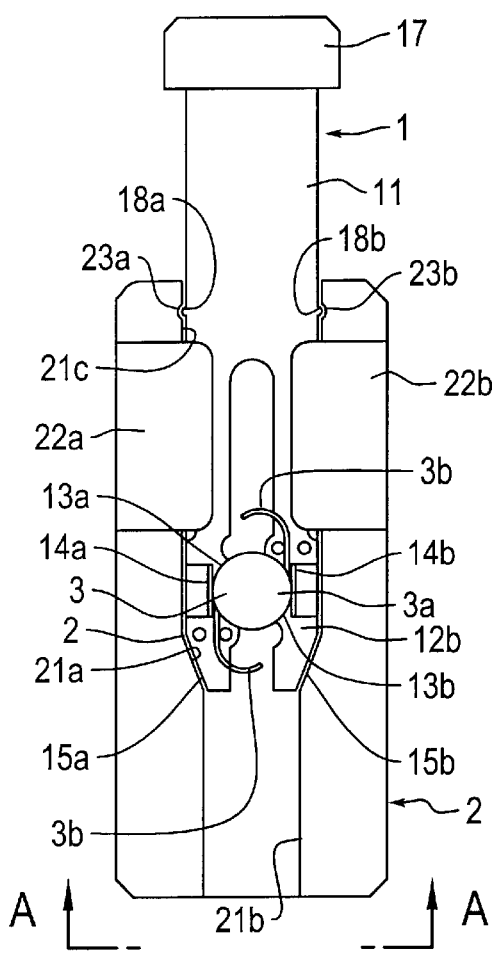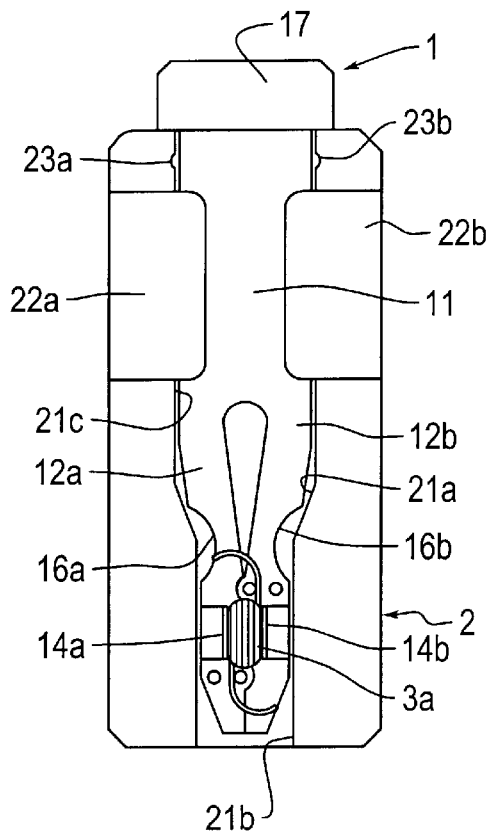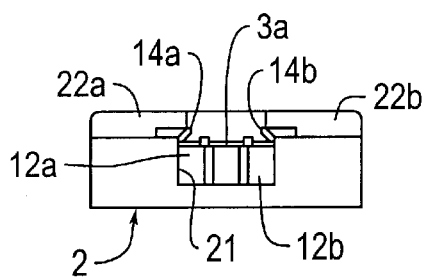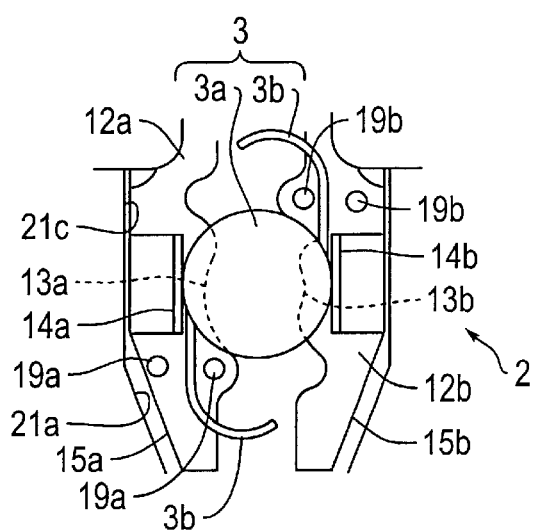
FIG. 2A
FIG. 2D
FIG. 2B
FIG. 2C

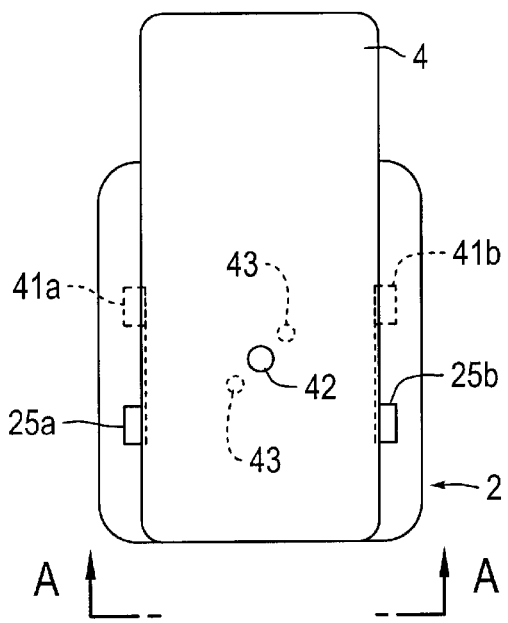
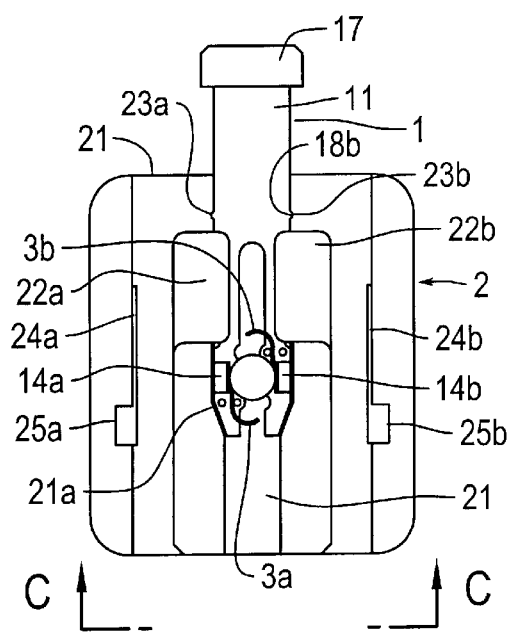
FIG. 3A
FIG. 3C
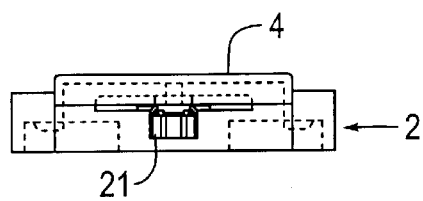
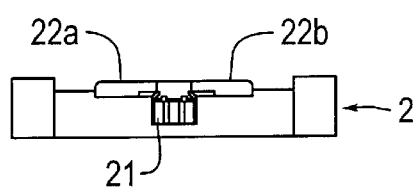
FIG. 3B
FIG. 3D

SOFT INTRAOCULAR LENS-FOLDING DEVICE AND STORAGE CASE

BACKGROUND OF THE INVENTION

1. Field of the Invention

The present invention relates to a soft intraocular lens-folding device for folding a soft intraocular lens used in cataract operations and the like, and to a soft intraocular lens storage case for storing this soft intraocular lens.

2. Description of the Related Art

For example, in a cataract operation, the aim is to restore sight by a surgical procedure, which inserts into the eye a soft intraocular lens, which is an artificial lens in place of a natural lens that has become opaque due to a cataract.

This soft intraocular lens has a circular optical lens portion, and a pair of supporting portions for stabilizing this optical lens portion inside the eye.

As this soft intraocular lens, there has been provided in recent years a soft intraocular lens, the optical lens portion of which is formed using silicon resin, acrylic resin, hydrogel, and other such materials.

By virtue of this soft intraocular lens, the optical lens portion can be deformed by being folded in two. In accordance therewith, in a case in which a soft intraocular lens is inserted Into the eye, the optical lens portion can be inserted in a folded state. Numerous clinical advantages can be derived as a result thereof, such as making the size of the incision smaller at the time of surgery, and faster recovery after surgery.

When using this soft intraocular lens, the optical lens portion must be folded beforehand prior to inserting the soft intraocular lens into the eye.

As methods for carrying out this folding operation, in the past there was a method, which makes use of a special forceps-shaped tool called an extractor, and a method, which makes use of a special jig called an injector.

In the method that uses an extractor, two extractors are used. That is, in this method, firstly, a first extractor is held in the right hand, and the center portion of the optical lens portion is clamped and held by this extractor. Next, in the as-is condition, this extractor is then switched to and held in the other hand, and a second extractor for intraocular insertion is hold in the freed up right hand, and the optical lens portion is folded using this second extractor. After confirming that the second extractor is holding the optical lens portion securely in a folded condition, the first extractor is removed. Thereafter, the soft intraocular lens being folded by the s second extractor is inserted into the eye.

In the method that uses an injector, firstly, after setting a soft intraocular lens inside an injector, the tip of that injector is inserted into the insertion part of the eye. Next, the extrusion aperture of the injector is operated, and the soft intraocular lens is inserted into the eye from the tip of the injector (publication of Japanese Patent application No. 4-212350, for example).

Furthermore, as a method other than the two methods described hereinabove, there has been proposed a method, which makes use of the soft intraocular lens folder disclosed in Published Japanese translation of PCT international publication for patent application No. 9-501574.

This soft intraocular lens folder is constituted such that 2 pairs of opposing jaws are formed respectively in a pair of pliers-shaped lever handles, and the edge of an optical lens portion is placed in and held by 4 supporting portions formed by these 2 pairs of jaws, and, in addition, by squeezing these lover handles, the gap of the pair of jaws of one side is made narrower, while at the same time, the gap of the pair of jaws of the other side is made wider.

If this tool is used, when the optical lens portion being held by the 2 pairs of jaws is folded by being put between the pair of jaws of the one side, it is possible to make the pair of jaws of the other side open and recede so as not to impede the folding thereof. In accordance therewith, folding can be performed with a soft intraocular lens being hold as-is.

However, the inventors have clearly shown that the above-mentioned respective 3 methods have the following problems.

That is, in the above-mentioned method in which 2 extractors are used, a problem is that operation is complicated, a problem is that it is difficult to accurately grasp the center of an optical lens portion, and a problem is that there is the danger of dropping a lens when switching an extractor from one hand to the other, and when re-grasping a lens. Another problem is that since the center portion of an optical lens portion is grasped and held by an extractor, the most important portion of a soft intraocular lens from the standpoint of optics is apt to be damaged by the extractor. Based an the above, the problem is that in surgery, in which quick, accurate actions are especially required, this method imposed a significant burden even on the skilled physician.

The above-mentioned method in which an injector is used appears at a glance to be simple and reliable. However, in actuality, if a soft intraocular lens is not set inside an injector precisely from the standpoint of the injector mechanism, there is the danger of the soft intraocular lens getting stuck inside the injector, and either not being able to be injected, or not being injected into the proper position. Therefore, with this method, a soft intraocular lens has to be set precisely inside an injector. However, with this method, the problem Is that it was not always easy to set a soft intraocular lens precisely inside an injector.

In the above-mentioned method in which a lens folder is used, two different operations, i.e. narrowing the gap of one side of the 2 pairs of jaws, while at the same time widening the gap of the other side must be carried out in concert. In accordance therewith, in this method, a problem is that the structure is complex, and it is apt to become very costly. Further, in this method, a problem is that, when folding an optical lens portion by manually operating the lever handle, if there is a mistake in the degree of force used in operating this handle, there is apt to be damage done to the optical lens portion by the application of unreasonable force to the optical lens portion. Furthermore, with this method, the folding of an optical lens portion must be carried out by holding the edge of the optical lens portion in the proper position over the 4 supporting portions formed by the 2 pairs of jaws. However, a problem is that this operation is also unexpectedly troublesome, and considerable concentration is required to perform this properly. This is because, if the optical lens portion holding position is inaccurate, not only is it not possible to fold the optical lens portion accurately, there is also the danger that the soft intraocular lens will slip off during folding.

An object of the present invention is to provide a soft intraocular lens-folding device and storage case, which have simple constitutions offering superb reliability and economical efficiency, and which are capable of performing handling and operating simply and reliably when holding and folding a soft intraocular lens.

SUMMARY OF THE INVENTION

To solve the above-mentioned problems, a soft intraocular lens-folding device of a first invention has (1)–(4) hereinbelow as characteristics:

(1) A movable member and a base member.

(2) A movable member comprises a pair of legs and a connecting portion. The pair of legs is made elastically bendable. The connecting portion has the function of connecting the pair of legs.

(3) A lens-receiving portion and a wall portion are disposed at the tips of the pair of legs. A soft intraocular lens is set astride both legs in the lens-receiving portion. The wall portion has the function of clamping a soft intraocular lens set in the lens-receiving portion.

(4) The base member comprises a slide groove portion. This slide groove portion is formed so as to allow the tips of the pair of legs to penetrate and slide through, and, in addition, to narrow the gap of the pair of legs in accordance with the extent of the movement thereof.

A second invention is characterized in that the first invention comprises a load-absorbing portion. This load-absorbing portion is disposed on the pair of legs. Further, this load-absorbing portion has the function of carrying out bending deformation by centrally absorbing the deformation load acting on the pair of legs in accordance with this pair of legs moving inside the slide groove portion.

A third invention is characterized in that the first invention comprises a positioning portion. This positioning portion has the function of positioning in a prescribed location in the sliding direction of the movable member a soft intraocular lens to be set in the lens-receiving portion.

A fourth invention is characterized in that the first invention comprises an orientation setting portion. This orientation setting portion has the function of setting the orientation of a soft intraocular lens set in the lens-receiving portion to a prescribed orientation in a direction of rotation with the central axis of this soft intraocular lens as the axis of rotation.

A fifth invention is characterized in that the first invention comprises a guide groove portion. This guide groove portion is disposed in the slide groove portion. Further, this guide groove portion has the function of guiding the parts of the pair of legs that are to the rear of the tips.

A sixth invention is characterized in that the first invention comprises a rise-up preventing portion. This rise-up preventing portion has the function of preventing the movable member from rising up out of the slide groove portion.

A seventh invention is characterized in that the first invention comprises a positioning portion. This positioning portion has the function of positioning the lens-receiving portion in a lens-receiving location that enables the setting of a soft intraocular lens in this lens-receiving portion.

An eighth invention is characterized in that the first invention comprises a positioning portion, This positioning portion has the function of positioning the lens-receiving portion in a lens-folding-completion position in which the folding of the above-mentioned soft intraocular lens set in this lens-receiving portion is completed.

A ninth invention is characterized in that the connecting portion of the first invention connects the base portion of the pair of legs.

A tenth invention is characterized in that the connecting portion of the first invention is integrally formed with the pair of legs.

To solve the above-mentioned problems, a soft intraocular lens storage case of an eleventh invention has (1)–(5) hereinbelow as characteristics.

(1) A movable member, a base member, and a lid member.

(2) A movable member comprises a pair of legs and a connecting portion. The pair of legs is made elastically bendable. The connecting portion has the function of connecting the pair of legs.

(3) A lens-receiving portion and a wall portion are disposed at the tips of the pair of legs. A soft intraocular lens is set astride both legs in the lens-receiving portion. The wall portion has the function of clamping a soft intraocular lens set in the lens-receiving portion.

(4) The base member comprises a slide groove portion. This slide groove portion is formed so as to allow the tips of the pair of legs to penetrate and slide through, and, in addition, to narrow the gap of the pair of legs in accordance with the extent of the movement thereof.

(5) The lid member forms a lens storage space for storing the above-mentioned soft intraocular lens set in the lens-receiving portion.

A twelfth invention is characterized in that the lens storage space of the eleventh invention is opened and closed by sliding the lid member.

A thirteenth invention is characterized in that the sliding direction of the lid member in the twelfth invention is set in the same direction as the sliding direction of the movable member.

A fourteenth invention is characterized in that the sliding direction of the lid member for opening the lens storage space in the thirteenth invention is set in the same direction as the sliding direction of the movable member for folding a soft intraocular lens.

A fifteenth invention is characterized in that the movable member and the lid member of the fourteenth invention are capable of sliding independently.

A sixteenth invention is characterized in that the movable member and the lid member of the fifteenth invention are capable of being slid and operated together.

A seventeenth invention is characterized in that the eleventh invention comprises a load-absorbing portion. This load-absorbing portion is disposed on the pair of legs. And this load-absorbing portion performs bending deformation by centrally absorbing the deformation load acting on the pair of legs in accordance with this pair of legs moving inside the slide groove portion.

An eighteenth invention is characterized in that the eleventh invention comprises a positioning portion. This positioning portion has the function of positioning in a prescribed location in the sliding direction of the movable member a soft intraocular lens to be set in the lens-receiving portion.

A nineteenth invention is characterized in that the eleventh invention comprises an orientation setting portion. This orientation setting portion has the function of setting the orientation of a soft intraocular lens set in the lens-receiving portion to a prescribed orientation in a direction of rotation with the central axis of this soft intraocular lens as the axis of rotation.

A twentieth invention is characterized in that the eleventh invention comprises a guide groove portion. This guide groove portion is disposed in the slide groove portion. And this guide groove portion has the function of guiding parts of the pair of legs that are to the rear of the tips.

A twenty-first invention is characterized in that the eleventh invention comprises a rise-up preventing portion. This rise-up preventing portion has the function of preventing the movable member from rising up out of the slide groove portion.

A twenty-second invention is characterized in that the eleventh invention comprises a positioning portion. This positioning portion has the function of positioning the lens-receiving portion in a lens-receiving location that enables the setting of a soft intraocular lens in this lens-receiving portion.

A twenty-third invention is characterized in that the eleventh invention comprises a positioning portion. This positioning portion has the function of positioning the lens-receiving portion in a lens-folding-completion position in which the folding of the above-mentioned soft intraocular lens set in this lens-receiving portion is completed.

A twenty-fourth invention is characterized in that the connecting portion of the eleventh invention connects the base portion of the pair of legs.

A twenty-fifth invention is characterized in that the connecting portion of the eleventh invention is integrally formed with the pair of legs.

A twenty-sixth invention is characterized in that the eleventh invention comprises the constitutions of the twelfth invention through the twenty-fifth invention.

A twenty-seventh invention is characterized in that the load-absorbing portion of the twenty-sixth invention is formed by partially narrowing the width of the legs.

BRIEF DESCRIPTION OF THE DRAWINGS

FIGS. 2(A)–2(D) are diagrams showing the constitution of a second aspect of the embodiment of a soft intraocular lens-folding device of the present invention;

FIGS. 3(A)–3(D) are diagrams showing the constitution of a first aspect of the embodiment of a soft intraocular lens storage case of the present invention, and diagrams showing a condition of prior to a soft intraocular lens being folded.

DETAILED DESCRIPTION OF THE PREFERRED EMBODIMENTS

Aspects of the embodiment of the present invention will be explained in detail hereinbelow by referring to the figures.

Figure 1A:
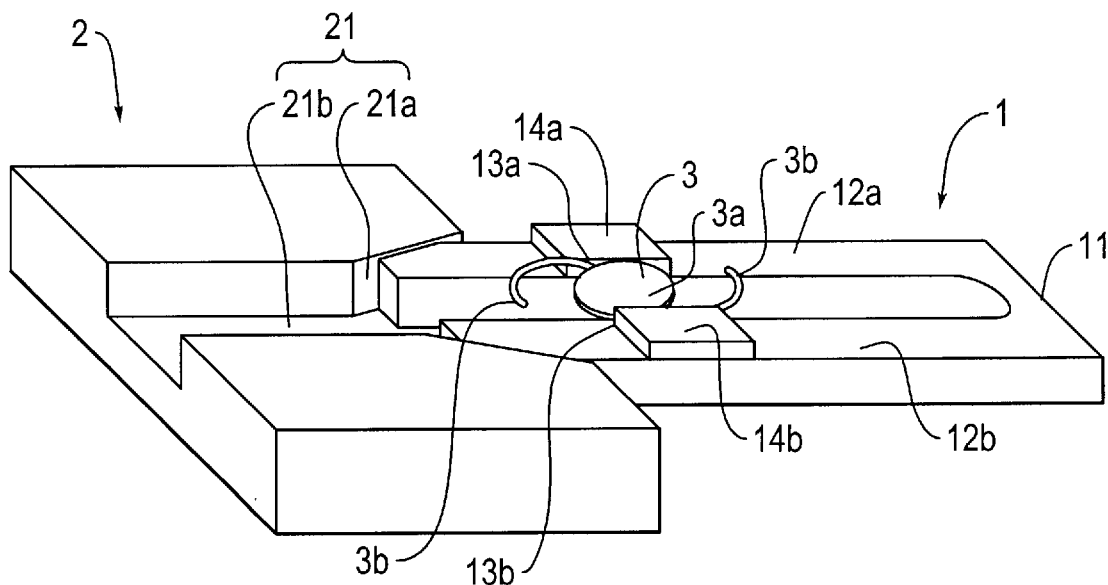
FIGS. 1(A) and 1(B) are oblique views showing the constitution of a first aspect of the embodiment of a soft intraocular lens-folding device of the present invention.
Figure 1B:
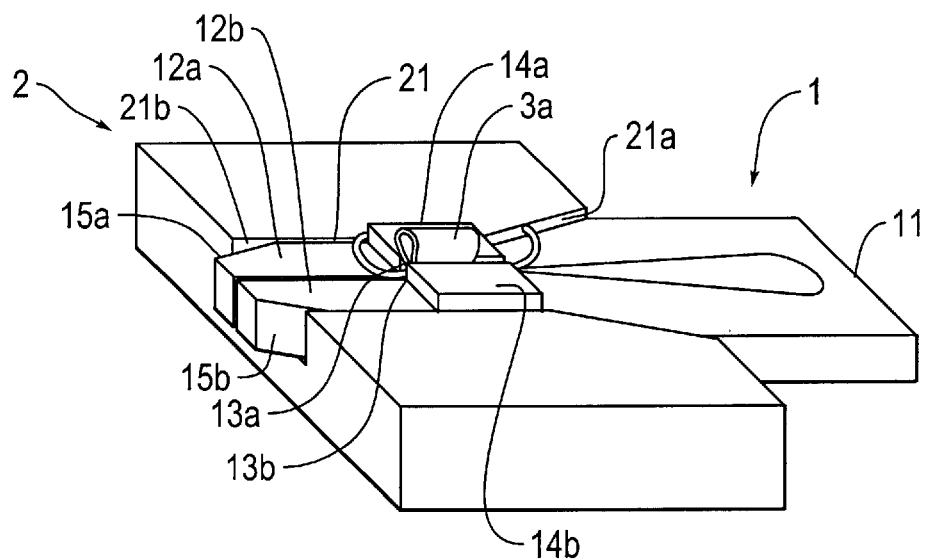

FIGS. 1(A) and 1(B) are oblique views showing different conditions of the constitution of a first aspect of the embodiment of a soft intraocular lens-folding device of the present invention.

First of all, the soft intraocular lens-folding device shown in the figure comprises a movable member 1 and a base member 2. The movable member 1 is constituted so as to have a rectangular cross-sectional shape. In accordance therewith, the movable member 1 comprises a pair of legs 12a, 12b, and a connecting portion 11, which connects this pair of legs 12a, 12b at a base portion. Hereinafter, this connecting portion 11 will be called a common base. This common base 11 as integrally formed with the legs 12a, 12b.

The above-mentioned legs 12a, 12b extend practically parallel in the same direction from the common base 11. These legs 12a, 12b are elastically bendable.

On the upper surface of the tips of these legs 12a, 12b, there are disposed lens-receiving portions 13a, 13b and wall portions 14a, 14b.

In the lens-receiving portions 13a, 13b, the optical lens portion 3a of a soft intraocular lens 3 is set horizontally. In this case, the optical lens portion 3a is set such that the edge thereof spans the pair of legs 12a, 12b.

The wall portions 14a, 14b have the function of horizontally clamping the edge of the optical lens portion 3a, which Is set in the lens-receiving portions 13a, 13b, when folding a soft intraocular lens 3. These wall portions 14a, 14b have opposing wall surfaces. These wall surfaces are inclined so as to draw near to one another as they head upward (an overhang condition). This is to prevent an optical lens portion 3a from slipping out of the wall portions 14a, 14b when folding an optical lens portion 3a.

On the tips of the legs 12a, 12b, tapered portions 15a, 15b are formed. These tapered portions 15a, 15b have the function of making operation smooth when the legs 12a, 12b interpenetrate a slide groove portion 21, which will be explained hereinbelow, and are made to slide inside the slide groove portion 21.

The base member 2 comprises a slide groove portion 21. The above-mentioned pair of legs 12a, 12b horizontally interpenetrate and slide in this slide groove portion 21. This slide groove portion 21 comprises a tapered groove portion 21a, and a parallel groove portion 21b. The tapered groove portion 21a is formed such that the groove width gradually narrows toward the direction of interpenetration of the legs 12a, 12b (hereinafter referred to as the "travelling direction"). The parallel groove portion 21b is formed so as to extend in the above-mentioned travelling direction from the head of the tapered groove portion 21a. In this case, the groove width of the parallel groove portion 21b is set so as to be practically the same groove width as the groove width at the head of the tapered groove portion 21a. In accordance therewith, the gap of the legs 12a, 12b becomes narrower as the legs 12a, 12b slide in the above-mentioned travelling direction. The movable member 1 and the bass member 2 are constituted by using a material that has appropriate degrees of elasticity and rigidity, such as, for example, a fluororesin, polyamide resin or aluminum. Furthermore, as this kind of material, resins, such as polyacrylate, polyethylene, polyethylene terephthalate, polyvinylchloride, polycarbonate, polysulfon, polystyrene, polybutylene terephthalate, polypropylene, and polymethylpentene, metals, such as duralmin, stainless steel, and titanium, or inorganic materials, such as ceramics can be used alone, or the above-mentioned resins, metals, and ceramics can be combined, and used as compounds.

The operation of the above-mentioned constitution will be explained.

A soft intraocular lens 3 comprises the above-mentioned optical lens portion 3a, and a supporting portion 3b. The optical lens portion 3a is formed in a circular shape. The supporting portion 3b has the function of stabilizing the optical lens portion 3b inside the eye. This supporting portion 3b is disposed on the edge of the optical lens portion 3a so as to form a pair of arms. Further, this supporting portion 3b is formed in the shape of an arc. Furthermore, this supporting portion 3b is extended so as to head outwardly from the optical lens portion 3a.

When folding the above-mentioned soft intraocular lens 3, firstly, as shown in FIG. 1(A), the optical lens portion 3a is set (set) in the lens-receiving portions 13a, 13b by an operator. This setting is performed such that the edge of the optical lens portion 3a uniformly spans both legs 12a, 12b.

In an aspect of the present invention, this positioning can be performed by simply placing the optical lens portion 3a inside the above-mentioned wall portions 14a, 14b. This is because the position of the soft intraocular lens 3 is defined by the wall portions 14a, 14b in a direction that is orthogonal to the sliding direction of the movable member 1. Further, this setting is performed such that the direction of extension of the supporting portion 3b coincides with the sliding direction of the movable member 1.

Next, the tips of the legs 12a, 12b, on which the soft intraocular lens 3 is set, are made to interpenetrate the slide groove portion 21 by an operator. Thereafter, the movable member 1 is made to slide in the travelling direction by the operator. In accordance with the sliding thereof, the legs 12a, 12b are elastically bent in directions that cause them to draw near to one another. In accordance therewith, the gap of the legs 12a, 12b is narrowed. As a result thereof, the optical lens portion 3a is clamped by the wall portions 14a, 14b. In accordance therewith, the optical lens portion 3a is folded. In this case the degree of bending of the legs 12a, 12b will depend on the degree of sliding thereof.

When the lens-receiving portions 13a, 13b reach the lens-folding-completion position by the sliding of the legs 12a, 12b, the sliding of the movable member 1 is halted. This is because, for example, when the lens-receiving portions 13a, 13b reach the lens-folding-completion position, the parts of the legs 12a, 12b to the tear of the tips hit against the walls in the vicinity of the boundary between the tapered groove portion 21a and the parallel groove portion 21b. In accordance therewith, the lens-receiving portions 13a, 13b are positioned in the lens-folding-completion position. As a result thereof, the optical lens portion 3a, as shown in FIG. 1(B), is folded into a prescribed condition. The folding of the optical lens portion 3a is completed by the above.

Furthermore, the lens-folding-completion position is the position in which the folding of an optical lens portion 3a is completed. This lens-folding-completion position, as shown in FIG. 1(B), is set inside the parallel groove portion 21b. That is, for example, this lens-folding-completion position is set in a position such that the legs 12a, 12b make practically complete contact.

According to this aspect of the embodiment explained in detail hereinabove, after setting an optical lens portion 3a in the lens-receiving portions 13a, 13b, the optical lens portion 3a can be folded by sliding the legs 12a, 12b under the guidance of the slide groove portion 21. In accordance therewith, an optical lens portion 3a can be reliably folded via a simple operation.

Further, according to this aspect of the embodiment, the main parts of the device can be constituted using a movable member 1 and a base member 2 of a simple structure. In accordance therewith, the device can be constructed simply, and at low cost. That is, the movable member 1 has a simple structure in which the cross-section is a simple rectangular shape. Further, the legs 12a, 12b and the common base 11 are integrally constituted. In accordance therewith, the movable member 1, for example, can be manufactured simply and at low cost by a single resin forming process (one shot forming). Similarly, the base member 2 has a simple structure that forms a slide groove portion 21 in the base material. In accordance therewith, this base member 2, for example, can be manufactured simply and at low cost by the single resin forming process (one shot forming) mentioned above. As a result thereof, according to this aspect of the embodiment, a soft intraocular lens-folding device can be manufactured simply and at low cost.

Furthermore, according to this aspect of the embodiment, when a soft intraocular lens 3 is set in the lens-receiving portions 13a, 13b, the soft intraocular lens 3 can be positioned by the pair of wall portions 14a, 14b in a prescribed position in a direction perpendicular to the sliding direction of the movable member 1. In accordance therewith, the position of the soft intraocular lens 3 in the above-mentioned direction can be reliably established.

Based on the above, according to this aspect of the embodiment, it is possible to provide a soft intraocular lens-folding device, which has a simple constitution offering superb reliability and economical efficiency, and which is capable of performing handling and operating simply and reliably when holding and folding a soft intraocular lens.

And furthermore, according to this aspect of the embodiment, a pair of legs 12a, 12b are connected together by a base portion. In accordance therewith, the length of the legs 12a, 12b can be shortened. As a result thereof, it is possible to make the device smaller.

Further, according to this aspect of the embodiment, wall surfaces of the pair of wall portions 14a, 14b are inclined so as to draw near to one another as they head upward. In accordance therewith, when folding an optical lens portion 3a, it is possible to prevent the optical lens portion 3a from slipping out of the wall portions 14a, 14b.

FIGS. 2(A)–2(D) are plan views and side views showing different conditions of the constitution of a second aspect of the embodiment of a soft intraocular lens-folding device of the present invention. Furthermore, in FIGS. 1(A) and 1(B) the same reference numerals will be assigned to parts that serve practically the same functions as those in the previous FIGS. 1(A) and 1(B) and a detailed explanation thereof will be omitted.

In FIG. 2(A) shows the condition of prior to folding a soft intraocular lens 3, FIG. 3(B) shows a side view of the device as seen in the direction of the arrows along line A—A shown in FIG. 2(A), FIG. 2(C) shows an exploded view of a portion of portion of FIG. 2(A), and FIG. 2(D) shows the condition in which a soft intraocular lens 3 has been folded.

A device of this aspect of the embodiment will be explained hereinbelow by focusing on the points of difference with the device of the first embodiment.

That is, in the device of this aspect of the embodiment, load-absorbing portions 16a, 16b are respectively disposed on the legs 12a, 12b. These load-absorbing portions 16a, 16b are disposed between the common base 11 and the lens-receiving portions 13a, 13b. These load-absorbing portions 16a, 16b have the function of centrally absorbing the deformation load acting on the legs 12a, 12b in line with the sliding of the movable member 1. These load-absorbing portions 16a, 16b are formed by making the legs 12a, 12b into a structure that facilitates localized elastic bending. The figure shows a case in which load-absorbing portions 16a, 16b are formed by making the width of the legs 12a, 12b locally narrower.

Further, in the device of this aspect of the embodiment, a guide groove portion 21c is also disposed in the slide groove portion 21 in addition to a tapered groove portion 21a, and a parallel groove portion 21b. This guide groove portion 21c has the function of guiding parts of the legs 12a, 12b to the rear of the tips.

Furthermore, in the device of this aspect of the embodiment, pressure guide portions 22a, 22b are provided on both borders of the guide groove portion 21c. These pressure guide portions 22a, 22b have the function of preventing the movable member 1 from rising up from the slide groove portion 21.

And furthermore, in the device of this aspect of the embodiment, the width of the common base 11 in the sliding direction is set so as to be wider than that of the previous aspect of the embodiment. This is for using the guide function of the guide groove portion 21c.

Further, in the device of this aspect of the embodiment, a stopper portion 17 is disposed at the rear portion of the movable member 1. This stopper portion 17 has the function of positioning the lens-receiving portions 13a, 13b in the lens-folding-completion position when the movable member 1 is made to slide in the travelling direction.

Furthermore, this stopper portion 17 is also used as a pressure knob for an operator to push the movable member 1.

Furthermore, in the device of this aspect of the embodiment, small protrusions 18a, 18b are disposed on both sides of the common base 11. These small protrusions 18a, 18b have the function of positioning the lens-receiving portions 13a, 13b in the lens setting position. Here, lens-receiving position refers to the position in which it is possible to set an optical lens portion 3a in the lens-receiving portions 13a, 13b. This position as shown in FIG. 2(A), is set inside the guide groove portion 21c. That is, this position is set in a position such that the legs 12a, 12b are practically not bent and deformed at all.

Locking grooves 23a, 23b are disposed on both sides of the guide groove portion 21c. The above-mentioned small protrusions 18a, 18b are mated to these locking grooves 23a, 23b when the lens-receiving portions 13a, 13b are positioned in the lens-receiving position. This state is shown in FIG. 2(A).

And furthermore, in the device of this aspect of the embodiment, a pair of perpendicular protruding portions 19a are disposed an the periphery of lens-receiving portion 13a on leg 12a as shown in FIG. 2(C). This pair of perpendicular protruding portions 19a is arranged so as to be slightly separated in a direction that is perpendicular to the sliding direction of the movable member 1. Similarly, a pair of perpendicular protruding portions 19b are disposed on the periphery of lens-receiving portion 13b on leg 12b as shown in FIG. 2(C).

The above-mentioned perpendicular protruding portions 19a, 19b are arranged so as to interpose the lens-receiving portions 13a, 13b therebetween. In the figure, there is shown a case in which the perpendicular protruding portions 19a of the one side are disposed in the travelling direction of the movable member 1 from the lens-receiving portions 13a, 13b, and the perpendicular protruding portions 19b of the other side are disposed in the opposite direction of the travelling direction (hereinafter referred to as the "reverse direction").

The above-mentioned perpendicular protruding portions 19a, 19b have the function of positioning a soft intraocular lens 3 in a prescribed position in the sliding direction of the movable member 1. This is because a soft intraocular lens 3 is set between the inner side of the perpendicular protruding portions 19a, 19b when set in the lens-receiving portions 13a, 13b. Moreover, this condition will hold a soft intraocular lens 3 even in a case in which, for example, the soft intraocular lens 3 is subjected to a shock. This is because even if a shock is applied to a soft intraocular lens 3, and the soft intraocular lens 3 attempts to move in the sliding direction of the movable member 1, the optical lens portion 3a collides with the inner sides of the perpendicular protruding portions 19a, 19b, and is prevented from moving.

Further, the above-mentioned perpendicular protruding portions 19a, 19b have the function of setting the orientation of a soft intraocular lens 3 in a prescribed orientation in the direction of rotation, which treats the central axis of the optical lens portion 3a as the axis of rotation. This is because, when a soft intraocular lens 3 is set in the lens-receiving portions 13a, 13b, the supporting portion 3b of the one side of the soft intraocular lens 3 is inserted between the corresponding pair of perpendicular protruding portions 19a, and the supporting portion 3b of the other side is inserted between the corresponding pair of perpendicular protruding portions 19b. Moreover, this condition will hold a soft intraocular lens 3 even in a case in which a shock is applied to the soft intraocular lens 3. This is because even if a shock is applied to a soft intraocular lens 3, and the soft intraocular lens 3 attempts to rotate in the above-mentioned direction of rotation, the supporting portions 3b collide with the inner sides of the perpendicular protruding portions 19a, 19b, and are prevented from moving.

The operation of the above-mentioned constitution will be explained.

When folding a soft intraocular lens 3, firstly, the lens-receiving portions 13a, 13b are positioned by an operator in the lens-receiving position. This is shown in FIG. 2(A). At this time, the small protrusions 18a, 18b are mated to the locking grooves 23a, 23b. In accordance therewith, the lens-receiving portions 13a, 13b are positioned in a semi-fixed condition in the lens-receiving position.

Next, a soft intraocular lens 3 is set in the lens-receiving portions 13a, 13b by an operator. At this time, the optical lens portion 3a is positioned by the wall portions 14a, 14b in a prescribed position orthogonally to the sliding direction of the movable member 1. Further, the optical lens portion 3a is positioned in a prescribed position in the sliding direction of the movable member 1. This is because the supporting portion 3b of the one side of the soft intraocular lens 3 is positioned between the corresponding pair of perpendicular protruding portions 19a, and the supporting portion 3b of the other side is positioned between the corresponding pair of perpendicular protruding portions 19b. Similarly, the orientation of the optical lens portion 3a is set at a prescribed orientation of the direction of rotation, which treats the central axis thereof as the axis of rotation.

Next, an operator pushes the stopper portion 17 in the travelling direction of the movable member 1. In accordance therewith, when the stopper portion 17 is pushed with a force greater than the mating force of the small protrusions 18a, 18b and the locking grooves 23a, 23b, the movable member 1 is made to slide in the travelling direction.

In accordance therewith, the pair of legs 12a, 12b are subjected to bending deformation by the tapered groove portion 21a. The deformation load acting on the legs 12a, 12b at this time is centrally absorbed by the load absorbing portions 16a, 16b. In accordance therewith, the folding load acting on the optical lens portion 3a is alleviated. Further, the gap of the pair of wall portions 14a, 14b is narrowed while maintaining a parallel condition. In accordance therewith, the optical lens portion 3a is folded accurately and stably along the centerline thereof.

Further, even if a soft intraocular lens 3 is subjected to a shock or the like during this sliding process, the soft intraocular lens 3 is positioned in a prescribed position, and, in addition, the orientation thereof is set to a prescribed orientation by the actions of the wall portions 14a, 14b and the perpendicular protruding portions 19a, 19b.

By so doing, when the lens-receiving portions 13a, 13b reach the lens-folding-completion position, the stopper portion 17 hits the rearward end portion of the base member 2. In accordance therewith, the sliding of the movable member 1 is stopped. As a result thereof, the lens-receiving portions 13a, 13b are positioned in the lens-receiving position. In accordance therewith, the folding of the optical lens portion 3a is completed. This situation is shown in FIG. 2(D).

According to this aspect of the embodiment explained hereinabove, when the movable member 1 is made to slide, the deformation load acting on the legs 12a, 12b thereof can be centrally absorbed by the load absorbing portions 16a, 16b. In accordance therewith, the folding load acting on the optical lens portion 3a can be alleviated.

Further, according to a constitution such as this, when folding an optical lens portion 3a, the gap of the wall portions 14a, 14b can be narrowed while accurately maintaining the parallel condition of both wall portions 14a, 14b. In accordance therewith, the optical lens portion 3a can be folded accurately along the centerline thereof. As a result thereof, the optical lens portion 3a can be stably and accurately folded without losing the optical functions thereof.

Further, according to this aspect of the embodiment, when the movable member 1 is made to slide, the parts to the rear of the tips of the legs 12a, 12b can be guided by the guide groove portion 21c. In accordance therewith, the side-to-side rolling of the movable member 1 can be prevented. As a result thereof, the movable member 1 can be made to slide stably.

Furthermore, according to this aspect of the embodiment, when the movable member 1 is made to slide, the movable member 1 can be prevented from rising up from the slide groove portion 21 by the pressure guide portions 22a, 22b. In accordance therewith, it is possible to prevent the movable member 1 from slipping out of the slide groove portion 21. As a result thereof, the movable member 1 can be made to slide stably.

And furthermore, according to this aspect of the embodiment, when the movable member 1 is made to slide in the travelling direction, the lens-receiving portions 13a, 13b can be positioned in the lens-folding-completion position by the stopper portion 17. In accordance therewith, the lens-receiving portions 13a, 13b can be prevented from going beyond the lens-folding-completion position despite the fact that the elasticity of the legs 12a, 12b has been weakened by the provision of the load absorbing portions 16a, 16b.

Further, according to this aspect of the embodiment, when the lens-receiving portions 13a, 13b reach the lens-receiving position, the movable member 1 is immobilized in a semi-fixed condition by the small protrusions 18a, 18b and the locking grooves 23a, 23b. In accordance therewith, in a case in which a shock is applied from externally to the movable member 1, it is possible to prevent an accident in which the movable member 1 slides in the travelling direction, and a soft intraocular lens 3 set in the lens-receiving portions 13a, 13b is damaged. Further, it is also possible to prevent an accident in which the movable member 1 moves in the reverse direction, and the movable member 1 falls out of the base member 2.

Furthermore, according to this aspect of the embodiment, when an optical lens portion 3a is set in the lens-receiving portions 13a, 13b, the optical lens portion 3a can be positioned by the perpendicular protruding portions 19a, 19b in a prescribed position in the sliding direction of the movable member 1. In accordance therewith, an optical lens portion 3a can be folded with uniform force about any point in the radial direction thereof.

And furthermore, according to this aspect of the embodiment, when an optical lens portion 3a is set in the lens-receiving portions 13a, 13b, the orientation of the optical lens portion 3a can be set in a prescribed orientation in the direction of rotation, which treats the central axis thereof as the axis of rotation. In accordance therewith, the optical lens portion 3a can be folded along a prescribed centerline that passes through the center thereof.

FIGS. 3(A)–3(D) and FIGS. 4(A)–4(C) are plan views and side views showing different conditions of constitutions of a first aspect of the embodiment of a soft intraocular lens storage case of the present invention. Furthermore, in FIGS. 3(A)–3(D) and FIGS. 4(A)–4(C), the same reference numerals will be assigned to parts that serve practically the same functions as those in the previous FIGS. 2(A)–2(D), and a detailed explanation thereof will be omitted.

The storage case shown in these figures provides a lid member 4 to the lens-folding device shown in FIGS. 2(A)–2(D), and is constituted such that a storage space is formed for storing a soft intraocular lens 3.

Figure 4A:
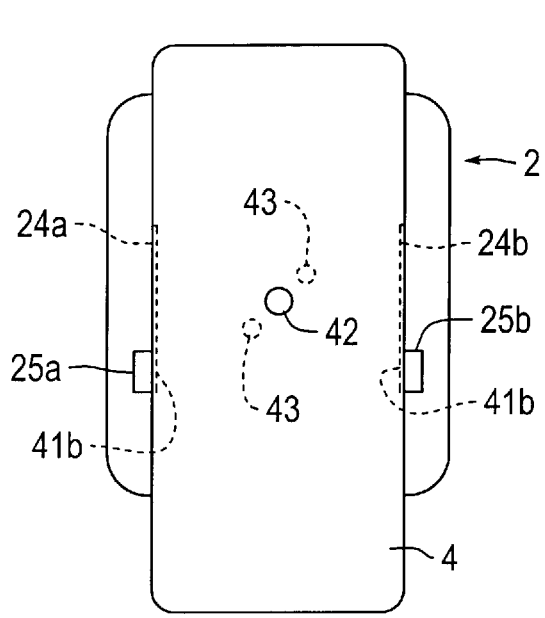
FIGS. 4(A)–4(C) are diagrams showing the constitution of a first aspect of the embodiment of a soft intraocular lens storage case of the present invention, and a diagram showing a condition of after a soft intraocular lens has been folded.
Figure 4B:
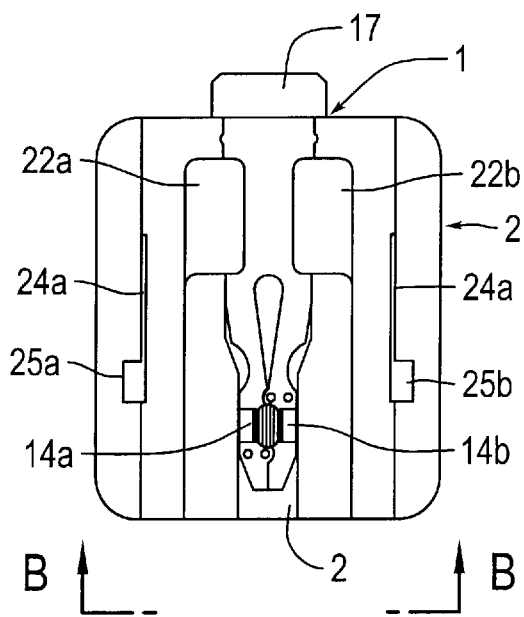
Figure 4C:
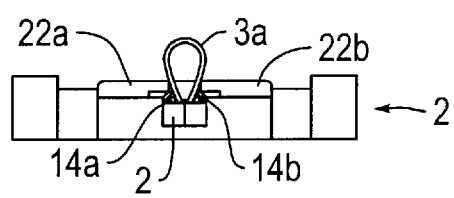

Here, FIGS. 3(A)–3(D) shows a condition in which a soft intraocular lens 3 is stored in a storage case, and FIGS. 4(A)–4(C) shows a condition in which a stored soft intraocular lens 3 is folded.

FIG. 3(A) shows a condition in which a lid member 4 is mounted, FIG. 3(B) shows a side view of the device as seen from the direction of the arrows along line A—A shown in FIG. 3(A), FIG. 3(C) shows a condition in which the lid member 4 has been removed, and FIG. 3(D) shows a side view of the device as seen from the direction of the arrows along line C—C shown in FIG. 3(C).

Further, in FIG. 4(A) shows a condition in which a lid member 4 is mounted, FIG. 4(B) shows a condition in which the lid member 4 has been removed, and FIG. 4(C) shows a side view of the device as seen from the direction of the arrows along line B—B shown in FIG. 4(B).

Furthermore, a portion of reference numerals concerning parts shared in common with FIGS. 2(A)–2(D) have been omitted in FIGS. 3(A)–3(D) and FIGS. 4(A)–4(C).

A soft intraocular lens storage case of this aspect of the embodiment comprises a movable member 1, a base member 2, and a lid member 4. The constitution of parts of the movable member 1 and base member 2 other than parts related to the lid member 3 are practically the same as those shown in FIGS. 2(A)–2(D). Therefore, detailed explanations of the parts thereof will be omitted in the explanation hereinbelow.

The above-mentioned lid member 4 is formed in the shape of a nearly rectangular plate. On this lid member 4, there is disposed a pair of latching protuberant portions 41a, 41b for mounting this lid member 4 to the base member 2. This pair of latching protuberant portions 41a, 41b is disposed on the side edge portions of the two long sides of the lid member 4, respectively.

In the above-mentioned base member 2, there is disposed a pair of latching groove portions 24a, 24b for holding the above-mentioned lid member 4 in a freely sliding manner. These latching groove portions 24a, 24b are formed in the sliding direction of the movable member 1.

In these latching groove portions 24a, 24b, there are disposed insertion opening portions 25a, 25b for mating the above-mentioned latching protuberant portions 41a, 41b to the latching groove portions 24a, 24b. These insertion opening portions 25a, 25b are disposed in the latching groove portions 24a, 24b in the end portions in the travelling direction of the movable member 1.

In the center portion of the above-mentioned lid member 4, there is disposed a lens-viewing window portion 42 for viewing the lens storage space from externally. Further, on the bottom surface of this lid member 4, there are formed support protruding portions 43a, 43b for forming the lens storage space.

Furthermore, the lid member 4 and the movable member 1 can slide independently of one another. However, both are designed so as to be able to be operated together. This is accomplished, for example, by setting the clearance in the up-down direction for both members to clearances that enable both members to be pushed by hand together.

The operation of the above-mentioned constitution will be explained.

Firstly, the operation for storing a soft intraocular lens 3 in the lens storage space will be explained.

In this case, first, the lens-receiving portions 13a, 13b are positioned by an operator in the lens-receiving position as shown in FIG. 3(C). Further, the operator removes the lid member 4 from the base member 2. Next, the operator sets a soft intraocular lens 3 in the lens-receiving portions 13a, 13b. Next, as shown in FIG. 2(A), the lens storage space is closed using the lid member 4. In accordance with the above, the operation for storing a soft intraocular lens 3 in a lens storage space is completed.

Here, the operation for closing the lens storage space using the lid member 4 will be explained. In this case, firstly, the latching protuberant portions 41a, 41b are inserted into the insertion opening portions 25a, 25b. Next, the lid member 4 is made to slide in the reverse direction of legs 12a, 12b. In accordance therewith, the lid member 4 is mounted to the base member 2. As a result thereof, the lens storage space is closed by the lid member 4.

Furthermore, the sliding of the lid member 4 is performed to end portion of the latching groove portions 24a, 24b. That Is, the sliding of the lid member 4 is performed until the end of the reverse direction of 12a, 12b of the movable member 1. In accordance therewith, the viewing window portion 42 is positioned in the lens-receiving position. As a result thereof, it is possible to view from externally via the viewing window portion 42 the soft intraocular lens 3 set in the lens-receiving portions 13a, 13b.

Further, the support protruding portion 43a of the one side is positioned so as to overlap with the corresponding pair of perpendicular protruding portions 19a. Similarly, the support protruding portion 43b of the other side is positioned so as to overlap with the corresponding pair of perpendicular protruding portions 19b. In accordance therewith, the supports for supporting the lid member 4 are formed by the support protruding portions 43a, 43b and the perpendicular protruding portions 19a, 19b. As a result thereof, the strength of the lid member 4 is reinforced. As a result thereof, the lens storage space can be stably maintained.

Further, in this case, the upper end portions of the pair of perpendicular protruding portions 19a of the one side are closed off by the support protruding portion 43a. Similarly, the upper end portions of the pair of perpendicular protruding portions 19b of the other side are closed off by the support protruding portion 43b. In accordance therewith, the supporting portion 3b of the one side of a soft intraocular lens 3 Is prevented from slipping out of the corresponding pair of perpendicular protruding portions 19a. Similarly, the supporting portion 3b of the other side is prevented from slipping out of the corresponding pair of perpendicular protruding portions 19b. As a result thereof, the position and orientation of a soft intraocular lens 3 is prevented from shifting even in a case in which the soft intraocular lens 3 is subjected to a shock.

Next, an operation for folding a soft intraocular lens 3, and removing same from the lens storage space will be explained.

This operation comprises an operation for opening the lens storage space, and an operation for folding a soft intraocular lens 3. In this aspect of the embodiment, these operations can be performed separately, and they can also be performed together.

Firstly, an operation of a case in which both operations are performed separately will be explained.

In this case, firstly, the lid member 4 is made to slide In the travelling direction of the movable member 1 by an operator. This sliding movement is carried out until the latching protuberant portions 41a, 41b reach the insertion opening portions 25a, 25b. When the latching protuberant portions 41a, 41b reach the insertion opening portions 25a, 25b, the sliding movement of the latching protuberant portions 41a, 41b is stopped. This is because the latching protuberant portions 41a, 41b hit against the walls of the insertion opening portions 25a, 25b. Next, the lid member 4 is raised from the base member 2 by the operator. In accordance therewith, the lens storage space is opened.

Next, the movable member 1 is made to slide in the travelling direction by the operator. This sliding movement is carried out until the stopper 17 hits against the rearward end portion of the base member 2. When the stopper 17 hits against the rearward end portion of the base member 2, the sliding movement of the movable member 1 is stopped. In accordance therewith, the lens-receiving portions 13a, 13b are positioned in the lens-folding-completion position. As a result thereof, the folding of the optical lens portion 3a is completed.

Next, the folded soft intraocular lens 3 is lifted from the lens-receiving portions 13a, 13b by the operator.

In accordance with the above, the operations for removing a soft intraocular lens 3 from the lens storage space is ended.

Next, an operation of a case in which an operation for opening the lens storage space, and an operation for folding a soft intraocular lens 3 are performed together will be explained.

In this case, firstly, the lid member 4 and the movable member 1 are pushed at the same time by an operator. In accordance therewith, the lid member 4 and the movable member 1 are made to slide in the travelling direction of the movable member 1. The sliding movement is carried out until the stopper 17 hits against the rearward end portion of the base member 2. In accordance therewith, an optical lens portion 3a is folded In a prescribed condition. Further, at this time, the latching protuberant portions 41a, 41b reach the insertion opening portions 25a, 25b.

Next, the lid member 4 is lifted from the base member 2 by the operator. In accordance therewith, the lens storage space is opened. Next, the folded soft intraocular lens 3 is lifted from the lens-receiving portions 13a, 13b by the operator.

In accordance with the above, the operation for removing a soft intraocular lens 3 from the lens storage space is ended.

According to this aspect of the embodiment explained in detail hereinabove, because a lens storage space for storing a soft intraocular lens 3 set in the lens-receiving portions 13a, 13b is formed by using a lid member 4, it is possible to handle the soft intraocular lens 3 set in the lens-receiving portions 13a, 13b in a condition in which same does not come in direct contact with the outside. In accordance therewith, when the soft intraocular lens 3 thereof is transported from the soft intraocular lens 3 manufacturer side to the user side, it is possible to carry the soft intraocular lens 3 in a condition in which same is set in the lens-receiving portions 13a, 13b. As a result thereof, it is possible to eliminate the trouble of setting a soft intraocular lens 3 in the lens-receiving portions 13a, 13b at the soft intraocular lens user side.

Further, according to this aspect of the embodiment, because the lens storage space is opened and closed by means of the sliding movement of a lid member 4, the open-close constitution of the lens storage space can be made simple.

Furthermore, according to this aspect of the embodiment, because the sliding direction of the lid member 4 is set to the same direction as the sliding direction of the movable member 1, it is possible to enhance the operability in a case in which an operator opens and closes the lens storage space, and a case in which a soft intraocular lens 3 is folded.

And furthermore, according to this aspect of the embodiment, because the sliding direction of the lid member 4 for opening the lens storage space is set to the same direction as the sliding direction of the movable member 1 for folding a soft intraocular lens 3, it is possible to make the soft intraocular lens storage case compact.

Further, according to this aspect of the embodiment, because the lid member 4 and the movable member 1 can be made to slide independently, it is possible to separately carry out an operation for opening the lens storage space, and an operation for folding a soft intraocular lens 3. In accordance therewith, it is possible to perform a soft intraocular lens 3 folding operation while confirming the folding condition thereof.

Furthermore, according to this aspect of the embodiment, because the lid member 4 and movable member 1 can be operated together, it is also possible to carry out the above-mentioned 2 operations at the same time as a single operation. In accordance therewith, It is possible to shorten the time from starting the folding of a soft intraocular lens 3 until removing the folded soft intraocular lens 3.

And furthermore, according to this aspect of the embodiment, because there is provided support protruding portions 43a, 43b, which coincide with the perpendicular protruding portions 19a, 19b, it is possible to reinforce the strength of the lid member 4. Further, it is also possible to maintain with certainty in a prescribed position and orientation the position and orientation of a soft intraocular lens 3. In accordance therewith, in a case in which a soft intraocular lens 3 is transported from the manufacturer side to the user side in a condition in which same is stored in the storage case, it is possible to prevent the soft intraocular lens 3 from slipping out of the lens-receiving portions 13a, 13b even if the soft intraocular lens 3 is subjected to a shock.

A plurality of aspects of the embodiment of the present invention has been explained hereinabove, but the present invention is not limited to the above-described aspects of the embodiment.

For example, in the above aspects of the embodiment, an explanation was given of a case in which the legs 12a, 12b and common base 11 are integrally formed. However, the present invention can also be constituted so as to be formed using different members.

Further, in the above aspects of the embodiment, an explanation was given of a case in which a pair of legs 12a, 12b is connected, and a case in which the pair of legs 12a, 12b is connected by a base portion. However, the present invention can also be constituted such that a pair of legs 12a, 12b is connected midway between a bass portion and the tips of the pair of legs 12a, 12b.

Furthermore, in the above aspects of the embodiment, an explanation was given of a case in which a load-absorbing portion is formed, and a case in which the load-absorbing portion is formed by making the width of the legs 12a, 12b locally narrower. However, the present invention can also be constituted such that the legs 12a, 12b, for example, are formed by making the materials and composition thereof differ locally.

And furthermore, in the above aspects of the embodiment, an explanation was given of a case In which the lid member 4 and the movable member 1 can slide independently. However, the present invention can also be constituted such that both the lid member 4 and the movable member 1 can slide by interlocking. That is, the present invention can be constituted such that when one side is made to slide, the other side also slides automatically by interlocking thereto. According to a constitution such as this, by an operation that makes one side slide, the other side can also be made to slide even if both are not operated together.

Further, according to the above aspects of the embodiment, an explanation was given of a case in which latching protuberant portions 41a, 41b, which constitute the sliding mechanism of the lid member 4, are disposed on the lid member 4, and latching groove portions 24a, 24b and insertion opening portions 25a, 25b are disposed on the base member 2. However, the present invention can also be constituted such that latching protuberant portions 41a, 41b are disposed on the base member 2, and latching groove portions 24a, 24b and insertion opening portions 25a, 25b are disposed on the lid member 4.

Furthermore, in the above aspects of the embodiment, an explanation was given of a case in which the sliding direction of the lid member 4 for opening the lens storage space is set in the same direction as the sliding direction of the movable member 1 for folding a soft intraocular lens 3. However, the present invention can also be constituted such that these sliding directions are set in opposing directions.

And furthermore, in the above aspects of the embodiment, an explanation was given of a case in which the sliding direction of the lid member 4 is set in the same direction as the sliding direction of the movable member 1. However, the present invention can also be constituted such that these sliding directions are set in different directions. For example, the present invention can be constituted such that these sliding directions are set orthogonally.

Further, in the above aspects of the embodiment, an explanation was given of a case in which the lid member 4 is mounted to the base member 2 in a freely detachable manner. However, the present invention can also be constituted such that the lid member 4 is permanently mounted to the base member 2.

Furthermore, in the above aspects of the embodiment, an explanation was given of a case in which the lens storage space is opened and closed by the slide constitution of the lid member 4. However, the present invention can also be constituted such that opening and closing is performed by a method other than this. For example, the present invention can be constituted such that the lens storage space opens and closes either by a detachable constitution that uses a hook mechanism, or by a rotating constitution that uses a hinge mechanism.

In addition thereto, the present invention naturally can have all sorts of variations and modifications of this embodiment within a scope that does not depart from the gist thereof.

As described in detail hereinabove, according to a first invention and an eleventh invention, after setting a soft intraocular lens in a lens-receiving portion, the soft intraocular lens can be folded by making the legs slide under the guidance of a slide groove portion. In accordance therewith, a soft intraocular lens can be reliably folded via a simple operation. Further, according to the first invention thereof, the main parts of the device can be constituted in accordance with a simply structured movable member and base member. In accordance therewith, the device can be manufactured easily and at low cost. Furthermore, according to the first invention thereof, when a soft intraocular lens is set in the lens-receiving portion, the soft intraocular lens can be accurately positioned by a pair of walls in a prescribed position in a direction that in orthogonal to the sliding direction of the movable member. In accordance therewith, the optical lens portion can be reliably folded along the centerline thereof.

Based on the above, according to the first invention, the constitution Is simple, and features outstanding reliability and economic efficiency, and handling and operation can be performed easily and with certainty when retaining and folding a soft intraocular lens.

Further, according to the second invention, the seventeenth invention, the twenty-sixth invention, and the twenty-seventh invention, when the movable member is made to slide, deformation load acting on the legs can be centrally absorbed by a load-absorbing portion. In accordance therewith, it is possible to alleviate the folding load placed on a soft intraocular lens, and, in addition, it is possible to stably and accurately fold the soft intraocular lens without losing the optical functions thereof.

Furthermore, according to the third invention, the eighteenth invention, the twenty-sixth invention, and the twenty-seventh invention, a soft intraocular lens set in the lens-receiving portion can be positioned in a prescribed position in the sliding direction of the movable member. In accordance therewith, it is possible for the optical lens portion to be folded with uniform force anywhere about the radial direction thereof.

And furthermore, according to the fourth invention, the nineteenth invention, and the twenty-sixth invention, the orientation of a soft intraocular lens set In the lens-receiving portion can be set to a prescribed orientation in a direction of rotation, with the central axis of the optical lens portion as the axis of rotation. In accordance therewith, it is possible to reliably fold the optical lens portion along a prescribed centerline.

Further, according to the fifth invention, the twentieth invention, and the twenty-sixth invention, when the movable member is made to slide, parts that are to the rear of the tips of the legs can be guided by a guide groove portion. In accordance therewith, because it is possible to prevent the side-to-side rolling of the movable member, the movable member can be made to slide stably.

Furthermore, according to the sixth invention, the twenty-first invention, and the twenty-sixth invention, when the movable member is made to slide, the movable member can be prevented from rising up out of the slide groove portion. In accordance therewith, it is possible to prevent the movable member from slipping out of the slide groove portion.

And furthermore, according to the seventh invention, the twenty-second invention, and the twenty-sixth invention, because there is provided a positioning portion for positioning the lens-receiving portion in the lens-receiving position, the lens-receiving portion can be prevented from moving from the lens-receiving position even in a case in which a shock is applied to the movable member.

Further, according to the eighth invention, the twenty-third invention, and the twenty-sixth invention, because there is provided a positioning portion for positioning the lens-receiving portion in the lens-folding-completion position when the movable member is made to slide in the travelling direction, the lens-receiving portion can be reliably positioned in the lens-folding-completion position.

Furthermore, according to the ninth invention, the twenty-fourth invention, and the twenty-sixth invention, because the pair of legs is connected at the base portion, the length of the legs can be shortened.

And furthermore, according to the tenth invention, the twenty-fifth invention, and the twenty-sixth invention, because the connecting portion is integrally formed with the legs, the movable member can be easily manufactured.

Further, according to the eleventh invention, because the storage space for storing a soft intraocular lens set in the lens-receiving portion is formed using a lid member, a soft intraocular lens set in the lens-receiving portion can be handled in a condition, wherein sane dots not make direct contact with the outside. In accordance therewith, when transporting a soft intraocular lens from the soft intraocular lens manufacturer side to the soft intraocular lens user side, it is possible to transport the soft intraocular lens in a condition, wherein same is set in the lens-receiving portion.

Furthermore, according to the twelfth invention, because the lens storage space is opened and closed by means of the sliding movement of the lid member, the open-close constitution of the lens storage space can be made simple.

And furthermore, according to the thirteenth invention, because the sliding direction of the lid member is set to the same direction as the sliding direction of the movable member, operability can be enhanced in a case in which an operator opens and closes the lens storage spaces and a case in which a soft intraocular lens is folded.

According to the fourteenth invention, because the sliding direction of the lid member for opening the lens storage space is set to the same direction as the sliding direction of the movable member for folding a soft intraocular lens, the soft intraoculr lens storage case can be made compact.

According to the fifteenth invention, because it is possible to make the lid member and the movable member slide independently, an operation for opening the lens storage space, and an operation for folding a soft intraocular lens can be performed separately. In accordance therewith, it is possible to carry out a soft intraocular lens folding operation while confirming the folding condition thereof.

According to the sixteenth invention, because it in possible to operate the lid member and the movable member at the same time, it is possible to perform the above-mentioned two operations together as a single operation.

What is claimed is:

1. A soft intraocular lens-folding device, comprising:
   a movable member, and
   a base member,
   wherein said movable member comprises an elastically bendable pair of legs, and a connecting portion for connecting said pair of legs,
   and at the tips of said pair of legs, there are disposed a lens-receiving portion for setting a soft intraocular lens astride both legs, and a wall portion for clamping said soft intraocular lens set in said lens-receiving portion,
   and said base member comprises a slide groove portion, which allows the tips of said pair of legs to penetrate and slide through said slide groove portion, and which, in addition, is formed so as to narrow the gap between said pair of legs in accordance with the extent of this sliding movement thereof.

2. The soft intraocular lens-folding device according to claim 1, comprising a load absorbing portion, which is disposed on said pair of legs, and which bends and deform by centrally absorbing the deformation load placed on said pair of legs by said pair of legs moving inside said slide groove portion.

3. The soft intraocular lens-folding device according to claim 1, comprising a positioning portion for positioning said soft intraocular lens set in said lens-receiving portion in a prescribed position in the sliding direction of said movable member.

4. The soft intraocular lens-folding device according to claim 1, comprising an orientation setting portion for setting the orientation of said soft intraocular lens set in said lens-receiving portion to a prescribed orientation in a direction of rotation, with the central axis of said soft intraocular lens as the axis of rotation.

5. The soft intraocular lens-folding device according to claim 1, comprising a guide groove portion, which is disposed in said slide groove portion, and which guides a part that is to the rear of the tips of said pair of legs.

6. The soft intraocular lens-folding device according to claim 1, comprising a rise-up preventing portion for preventing said movable member from rising up out of said slide groove portion.

7. The soft intraocular lens-folding device according to claim 1, comprising a positioning portion for positioning said lens-receiving portion in a lens-receiving position, which enables said soft intraocular lens to be set in said lens-receiving portion.

8. The soft intraocular lens-folding device according to claim 1, comprising a positioning portion for positioning said lens-receiving portion in a lens-folding-completion position in which the folding of said soft intraocular lens set in said lens-receiving portion is completed.

9. The soft intraocular lens-folding device according to claim 1, wherein said connecting portion connects the base of said pair of legs.

10. The soft intraocular lens-folding device according to claim 1, wherein said connecting portion is integrally formed with said pair of legs.

11. A soft intraocular lens storage case, comprising:
   a movable member;
   a base member; and
   a lid member,
      wherein said movable member comprises an elastically bendable pair of legs, and a connecting portion for connecting said pair of legs,
      and at the tips of said pair of legs, there are formed a lens-receiving portion for setting a soft intraocular lens astride both legs, and a wall portion for clamping said soft intraocular lens set in said lens-receiving portion,
      said base member comprises a slide groove portion, which allows the tips of said pair of legs to penetrate and slide through said slide groove portion, and which, in addition, is formed so as to narrow the gap between said pair of legs in accordance with the extent of the sliding movement thereof,
      and said lid member forms a lens storage space for storing said soft intraocular lens set in said lens-receiving portion.

12. The soft intraocular lens storage case according to claim 11, wherein said lens storage space opens and closes by means of a sliding movement of said lid member.

13. The soft intraocular lens storage case according to claim 12, wherein the sliding direction of said lid member is set in the same direction as the sliding direction of said movable member.

14. The soft intraocular lens storage case according to claim 13, wherein the sliding direction of said lid member for opening said lens storage space is set in the same direction as the sliding direction of said movable member for folding said soft intraocular lens.

15. The soft intraocular lens storage case according to claim 14, wherein said movable member and said lid member are independently slidable.

16. The soft intraocular lens storage case according to claim 15, wherein said movable member and said lid member an be operated together.

17. The soft intraocular lens storage case according to claim 11, comprising a load absorbing portion, which is disposed on said pair of legs, and which bends and deforms by centrally absorbing the deformation load placed on said pair of legs by said pair of legs moving inside said slide groove portion.

18. The soft intraocular lens storage case according to claim 11, comprising a positioning portion for positioning said soft intraocular lens set in said lens-receiving portion in a prescribed position in the sliding direction of said movable member.

19. The soft intraocular lens storage case according to claim 11, comprising an orientation setting portion for setting the orientation of said soft intraocular lens set in said lens-receiving portion to a prescribed orientation in a direction of rotation, with the central axis of said soft intraocular lens as the axis of rotation.

20. The soft intraocular lens storage case according to claim 11, comprising a guide groove portion, which is disposed in said slide groove portion, and which guides a part that is to the rear of the tips of said pair of legs.

21. The soft intraocular lens storage case according to claim 11, comprising a rise-up preventing portion for preventing said movable member from rising up out of said slide groove portion.

22. The soft intraocular lens storage case according to claim 11, comprising a positioning portion for positioning said lens-receiving portion in a lens-receiving position which enables said soft intraocular lens to be set in said lens-receiving portion.

23. The soft intraocular lens storage case according to claim 11, comprising a positioning portion for positioning said lens-receiving portion in a lens-folding-completion position in which the folding of said soft intraocular lens is completed.

24. The soft intraocular lens storage case according to claim 11, wherein said connecting portion connects the base of said pair of legs.

25. The soft intraocular lens storage case according to claim 11, wherein said connecting portion is integrally formed with said pair of legs.

26. The soft intraocular lens storage case according to claim 11, comprising:
   a load absorbing portion, which is disposed on said pair of legs, and which bends and deforms by centrally absorbing the deformation load placed on said pair of legs by said pair of legs moving inside said slide groove portion;
   a positioning portion for positioning said soft intraocular lens set in said lens-receiving portion in a prescribed position in the sliding direction of said movable member;
   an orientation setting portion for setting the orientation of said soft intraocular lens set in said lens-receiving portion to a prescribed orientation in a direction of rotation, with the central axis of said soft intraocular lens as the axis of rotation;

a guide groove portion, which is disposed in said slide groove portion, and which guides a part that is to the rear of the tips of said pair of legs;

a rise-up preventing portion for preventing said movable member from rising up out of said slide groove portion;

a positioning portion for positioning said lens-receiving portion in a lens-receiving position which enables said soft intraocular lens to be set in said lens-receiving portion; and a positioning portion for positioning said lens-receiving portion in a lens-folding-completion position in which the folding of said soft intraocular lens is completed, wherein said connecting portion is integrally formed with said pair of legs so as to connect the base of said pair of legs, said lens storage space opens and closes by means of a sliding movement of said lid member, and the sliding direction of said lid member is set in the same direction as the sliding direction of said pair of legs, the sliding direction of said lid member for opening said lens storage space is set in the same direction as the sliding direction of said movable member for folding said soft intraocular lens, said pair of legs and said lid member are independently slidable, and said pair of legs and said lid member can be operated together.

27. The soft intraocular lens storage case according to claim 26, wherein said load-absorbing portion is formed by locally narrowing the width of said legs.

* * * * *

UNITED STATES PATENT AND TRADEMARK OFFICE
CERTIFICATE OF CORRECTION

PATENT NO.   : 6,386,357 B1
DATED        : May 14, 2002
INVENTOR(S)  : Yoshikazu Egawa et al.

It is certified that error appears in the above-identified patent and that said Letters Patent is hereby corrected as shown below:

Title page,
Item [22], PCT Filed: should read -- July 12, 2000 --

Column 18,
Line 67, change "this" to -- the --.

Column 19,
Line 3, change "deform" to -- deforms --.

Column 20,
Line 13, change "an" to -- can --.

Signed and Sealed this

First Day of October, 2002

Attest:

Attesting Officer

JAMES E. ROGAN
Director of the United States Patent and Trademark Office